United States Patent
Brahm et al.

(10) Patent No.: US 8,445,623 B2
(45) Date of Patent: May 21, 2013

(54) PROCESS FOR THE PREPARATION OF POLYISOCYANATES WITH A BIURET STRUCTURE

(75) Inventors: Martin Brahm, Odenthal (DE); Dieter Mager, Leverkusen (DE); André Fellhoelter, Bergisch Gladbach (DE); Reinhard Halpaap, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 235 days.

(21) Appl. No.: 12/861,306

(22) Filed: Aug. 23, 2010

(65) Prior Publication Data

US 2011/0046300 A1    Feb. 24, 2011

(30) Foreign Application Priority Data

Aug. 21, 2009 (DE) .......................... 10 2009 038 463

(51) Int. Cl.
*C08G 18/32* (2006.01)
(52) U.S. Cl.
USPC .............................. 528/68; 560/335; 560/336
(58) Field of Classification Search
USPC ...................................... 560/335, 336; 528/68
See application file for complete search history.

(56) References Cited

U.S. PATENT DOCUMENTS 4,837,359 A    6/1989 Woynar et al.
6,720,400 B2 *  4/2004 Halpaap et al. ................. 528/48

FOREIGN PATENT DOCUMENTS

| DE | 1101394 B | | 3/1961 |
| EP | 277353 A1 | | 8/1988 |
| EP | 1158013 A1 | | 11/2001 |
| WO | WO-2008/110492 | * | 9/2008 |
| WO | WO-2008/110492 A1 | | 9/2008 |

OTHER PUBLICATIONS

WO-2008/110492 English Translation.*
Laas et al., "The Synthesis of Aliphatic Polyisocyanates Containing Biuret, Isocyanurate or Uretdione Backbones for Use in Coatings", J. Prakt. Chem., vol. 336, pp. 185-200 (1994).

* cited by examiner

*Primary Examiner* — Michael L Leonard
(74) *Attorney, Agent, or Firm* — Novak Druce Connolly Bove + Quigg LLP

(57) ABSTRACT

The present invention relates to an improved process for the preparation of polyisocyanates with a biuret structure by continuous reaction of excess amounts of organic diisocyanates having exclusively aliphatically and/or cycloaliphatically bonded isocyanate groups with organic diamines having exclusively aliphatically and/or cycloaliphatically bonded primary amino groups at elevated temperatures by 2-stage addition of the isocyanate component.

12 Claims, No Drawings

PROCESS FOR THE PREPARATION OF POLYISOCYANATES WITH A BIURET STRUCTURE

RELATED APPLICATIONS

This application claims benefit to German Patent Application No. 10 2009 038 463.4, filed Aug. 21, 2009, which is incorporated herein by reference in its entirety for all useful purposes.

BACKGROUND OF THE INVENTION

The present invention relates to an improved process for the preparation of polyisocyanates with a biuret structure by continuous reaction of excess amounts of organic diisocyanates having exclusively aliphatically and/or cycloaliphatically bonded isocyanate groups with organic diamines having exclusively aliphatically and/or cycloaliphatically bonded primary amino groups at elevated temperatures by 2-stage addition of the isocyanate component. Polyisocyanates prepared in this way are distinguished by a high stability, can be prepared with a high space/time yield and have a low content of by-products. In a given production installation, process variants for obtaining biuret polyisocyanates with required target parameters (viscosity, NCO content) are possible in a simple manner.

The preparation of aliphatic polyisocyanates with biuret structures has been known since 1958, (DE-A 1101394). Further possible preparation processes are described in a review article (Laas et al., J. prakt. Chem. 336, 1994, 185-200) which discusses the advantages and disadvantages of the particular processes.

A distinction is made in principle between two process groups: on the one hand the so-called water processes, in which the diisocyanates are reacted with excess amounts of water to give ureas, and these are subsequently reacted with excess amounts of diisocyanates to give biurets, and on the other hand the so-called diisocyanate/diamine processes, in which urea is prepared directly from isocyanate and a deficient amount of amine and the biuret is subsequently prepared in turn with an excess of diisocyanate. As stated in the review article cited above (Laas et al.), numerous variants have been developed and described for both processes. In the processes described, predominantly hexamethylene-diisocyanate (HDI) and optionally hexamethylenediamine (HDA) are used for the preparation of industrially the most important HDI biurets, the biurets initially obtained, which are present as a solution in excess diisocyanate, being freed from the excess diisocyanate by distillation and/or extraction and isolated as low-monomer biuret polyisocyanates.

Biuret polyisocyanates prepared by the water process are as a rule distinguished by a good monomer stability, i.e. stability towards partial cleavage back into free diisocyanates, good dilutabilities, i.e. stability of dilute solutions with respect to clouding and precipitates under the action of moisture, and outstanding colour numbers because of the relatively mild conditions during the preparation. In the biuretization reactions by the water process, however, due to the principle of the process some of the isocyanate groups contained in the starting mixture are always converted intermediately into amino groups by reaction with a biuretizing agent. Since the isocyanate groups used up in this way have originally once been prepared by phosgenation of amino groups, this procedure seems expensive and not very economical. Furthermore, gaseous or liquid by-products are formed in these known processes, such as, for example, carbon dioxide, carbon monoxide, carbon oxysulfide, olefins or nitriles, which, with the exception of the anhydrides obtained in the pivalic acid/water process, are not recyclable and must be disposed of.

In the diisocyanate/diamine processes which have been developed, the advantage of the economical preparation manifests itself with no or only little formation of by-products, and no isocyanate groups prepared from amino groups by phosgenation are converted back into amino groups and subsequently urea groups and biuret groups. These processes have likewise been constantly developed further to a high quality level, as described e.g. in EP-A 277353. It was possible for a reduced monomer and dilution stability to be improved further by further optimizations, as described in EP-B 1158013.

As described in the literature available, HDI is preheated to temperatures of approx. 230-250° C. and reacted with HDA in a mixing chamber. During this procedure, the temperature increases further to values of typically 270-280° C. Thereafter, the temperature is cooled in stages as rapidly as possible to e.g. 180° C. In order to avoid an unnecessarily high degree of pre-damage to the heat-sensitive HDI, the educt is heated up and then overheated in the shortest possible time. In principle, however, it is not possible to rule out heat damage completely.

In order to ensure a fast reaction and biuret formation, specific mixing chamber/nozzle systems are employed for optimum and fast mixing of the isocyanate component and amine component. For flow reasons, these systems are designed for a narrow mass flow range and are therefore limited in variation. This optimum range is departed from during load changes and product change-over. The non-ideal mixing leads to a delayed and poorer biuret formation and larger urea crystals, with the consequence that the total reaction time is prolonged and side reactions increase.

From environmental aspects, heating of the large mass flows of HDI and HDA to high temperatures with the likewise necessary subsequent rapid cooling leads to a high energy consumption with a high potential of carbon dioxide emission.

The object of the present invention was therefore to obtain polyisocyanates with a biuret structure by the economically favourable diisocyanate/diamine process without exposing the diisocyanate for too long at too high a temperature, and to operate the preparation always with the optimum mixing conditions from the mixing elements during load or product change-overs. The object of the invention was in particular also to lower the high energy consumption for heating the diisocyanate stream compared with the normal process, without eliminating the proven advantages of the diisocyanate/diamine process.

EMBODIMENTS OF THE INVENTION

An embodiment of the present invention is a process for continuously preparing a polyisocyanate comprising a biuret structure comprising continuously reacting an excess amount of an organic isocyanate (A) comprising exclusively aliphatically and/or cycloaliphatically bonded isocyanate groups with an organic amine (B) comprising exclusively aliphatically and/or cycloaliphatically bonded primary amino groups by a) mixing a first amount of said organic isocyanate (A) with said organic amine (B) at a temperature above 170° C. to form a reaction mixture stream, and b) metering a second amount of said organic isocyanate (A) at a temperature in the range of from 20 to 250° C. into said reaction mixture stream of a), wherein the ratio of the parts by weight of said organic isocyanate (A) fed per unit time into step a) to the parts by weight of said organic isocyanate (A) fed per unit time into b) is in the range of from 1:9 to 9:1, and the ratio of the total number of NCO groups fed per unit time into both steps a) and b) to the number of $NH_2$ groups fed in per unit time into step a) is at least 4:1.

Another embodiment of the present invention is the above process, wherein said organic isocyanate (A) comprises HDI.

Another embodiment of the present invention is the above process, wherein said organic amine (B) comprises HDA.

Another embodiment of the present invention is the above process, the ratio of the total number of NCO groups fed per unit time into both steps a) and b) to the number of $NH_2$, groups fed in per unit time into step a) is in the range of from 18:1 to 25:1.

Another embodiment of the present invention is the above process, ratio of the parts by weight of said organic isocyanate (A) fed per unit time into step a) to the parts by weight of said organic isocyanate (A) fed per unit time into b) is in the range of from 5:5 to 7.5:2.5.

Another embodiment of the present invention is the above process, wherein said first amount of said organic isocyanate (A) in step a) is preheated to a temperature in the range of from 200 to 240° C. before it is mixed with said organic amine (B).

Another embodiment of the present invention is the above process, wherein the temperature in step a) is maintained in the range of from 230 to 320° C.

Another embodiment of the present invention is the above process, wherein said second amount of said organic isocyanate (A) in step b) has a temperature below that of said first amount of said organic isocyanate (A) in step a).

Another embodiment of the present invention is the above process, wherein said process is carried in the presence of a catalyst.

Another embodiment of the present invention is the above process, wherein said catalyst comprises one or more acids or mixtures thereof.

Another embodiment of the present invention is the above process, wherein said catalyst comprises di-n-butyl phosphate.

Another embodiment of the present invention is the above process, wherein said polyisocyanate comprising a biuret structure is purified from excess monomeric diisocyanate via extraction or thin film distillation resulting in a monomeric diisocyanate content of less than 0.5 wt. %.

Yet another embodiment of the present invention is a polyisocyanate comprising a biuret structure obtained by the above process.

Yet another embodiment of the present invention is a two-component polyurethane paint prepared from the polyisocyanate mentioned above.

Yet another embodiment of the present invention is a substrate coated with a coating obtained from the two-component polyurethane paint described above.

DESCRIPTION OF THE INVENTION

As has now been found, surprisingly, it is possible to obtain, in a continuous process, high-quality polyisocyanates with a biuret structure which are based on organic isocyanates having exclusively aliphatically and/or cycloaliphatically bonded isocyanate groups with organic amines having exclusively aliphatically and/or cycloaliphatically bonded primary amino groups under a reduced exposure to heat compared with the prior art and without departing from the optimum conditions during a load and product change, with a reduced energy input, by carrying out the reaction in two stages as described in the following.

The present invention therefore relates to a process for the continuous preparation of polyisocyanates with a biuret structure by continuous reaction of excess amounts of organic isocyanates containing exclusively aliphatically and/or cycloaliphatically bonded isocyanate groups (A) with organic amines containing exclusively aliphatically and/or cycloaliphatically bonded primary amino groups (B) by a) mixing a first amount of the isocyanate component A with the amine component B, during which the temperature is kept above 170° C., and b) metering a second amount of the isocyanate component A with a temperature of from 20 to 250° C. into the stream of the reaction mixture resulting from step a), wherein the ratio of the parts by weight of the isocyanate component A fed per unit time into stage a) to b) is 1:9 to 9:1, and the number of NCO groups fed per unit time in total into a) and b) to the number of $NH_2$ groups fed in per unit time is at least 4:1.

At the high reaction temperatures of above 170°, a direct reaction takes place between isocyanate groups and amine groups in an equilibrium reaction to give urea structures and biuret structures. Depending on the reaction temperature set and the isocyanate excess used, the equilibrium here is almost completely on the side of the urea and biuret.

The total amount of diisocyanate, part amount from stage a) and part amount from stage b), to the amount of amine reacted in stage a) is chosen such as is hitherto conventional in the one-stage diisocyanate/diamine process for obtaining a biuret polyisocyanate with the required characteristic data.

Surprisingly, the significantly reduced ratio of isocyanate component to amine component during the mixing operation in stage a), compared with the one-stage process, does not lead to another (conventionally higher-viscosity) product with a lower NCO content. This is all the more surprising since precisely the isocyanate/amine reaction takes place instantaneously at the high reaction temperatures, which manifests itself in the high exothermicity directly during the mixing, which has the effect of heating up the product stream by approx. 20 to 80° C.

It was accordingly not to be expected at all that the 2-stage procedure according to the invention in the diisocyanate/diamine process leads to the same products as a direct one-stage metering of the amine component to the total isocyanate component.

In the two-stage procedure, heating up of the 1st isocyanate stream to a lower temperature compared with the one-stage procedure is sufficient to achieve the necessary mixing and reaction temperature. Regardless of load and product change, the actual mixing operation on the isocyanate and amine component can be carried out with always the same mass flows of isocyanate and amine. The remainder of the isocyanate component, the second part amount, is metered in subsequently without the characteristic data of the finished product prepared changing. Since the reaction enthalpy liberated heats up a smaller mass flow in step a) according to the invention compared with the one-stage procedure, the required reaction temperature is achieved with a comparatively low amount of preheated isocyanate component A. A further significant reduction in the energy requirement results due to the preheating temperature for the isocyanate component A conventionally being reduced once more in step b) during the metering in the case according to the invention. The isocyanate overall is exposed to heat to a lesser extent. This leads to the reduction in the formation of by-products.

Starting materials for the process according to the invention are organic diisocyanates having exclusively aliphatically and/or cycloaliphatically bonded isocyanate groups and a molecular weight of below 300. Examples of such diisocyanates are 1,4-diisocyanatobutane, 1,6-diisocyanatohexane (hexamethylene-diisocyanate, HDI), 1,6-diisocyanato-2,2,4-trimethylhexane and/or 1,6-diisocyanato-2,4,4-trimethylhexane, 1,4- and/or 1,5-diisocyanatohexane, 2,6-diisocyanatohexanoic acid ethyl ester, 1,9-diisocyanatononane, 1,12-diisocyanatododecane, 1,4-diisocyanatocyclohexane, 2,4- and/or 2,6-diisocyanato-1-methylcyclohexane, 1-isocyanato-3,3,5-trimethyl-5-isocyanatomethylcyclohexane (isophorone-diisocyanate, IPDI), 1,3- and/or 1,4-bis(isocyanatomethyl)cyclohexane, 2,4'- and/or 4,4'-diisocyanatodicyclohexylmethane or 6-isocyanatohexanoic acid 2-isocyanatoethyl ester. Any desired mixtures of such diisocyanates can likewise be used. 1,6-Diisocyanatohexane (HDI) is preferred.

Further starting materials for the process according to the invention are organic diamines having exclusively aliphatically and/or cycloaliphatically bonded primary amino groups. They have a molecular weight of below 300. Examples are 1,2-diaminoethane, 1,2-diaminopropane, 1,3-diaminopropane, 1,4-diaminobutane, 1,6-diaminohexane (hexamethylenediamine, HDA), 1,6-diamino-2,2,4-trimethylhexane and/or 1,6-diamino-2,4,4-trimethylhexane, 1,4- and/or 1,5-diaminohexane, 2,4-and/or 2,6-diamino-1-methylcyclohexane, 1-amino-3,3,5-trimethyl-5-aminomethylcyclohexane (isophoronediamine, IPDA), 1,3- and/or 1,4-bis(aminomethyl)cyclohexane or 2,4'- and/or 4,4'-diaminodicyclohexylmethane. Any desired mixtures of such diamines can likewise be employed. 1,6-Diaminohexane (HDA) is preferred.

In principle in order to reduce the functionality of the biuretpolyisocyanate it is possible to use in parts monoamines beside the aforementioned diamines. This is not preferred. But if monomamines are used they are mixed with diamines up to 30 equivalent-%, preferably up to 20 equivalent-%, more preferably up to 10 equivalent-% relating to the sum of equivalents of diamines and monoamines. If monoamines are used aliphatic and/or cycloaliphatic primary amines with a molecular weight of at most 185 are used, as for example methyl amine, ethyl amine, propyl amine, butyl amine, pentyl amine, hexyl amine, octylamine, dodecyl amine, cyclohexyl amine or their respective isomers. These amines can be used in any mixtures among each other or with the used diamines.

In carrying out the process according to the invention, the starting isocyanates and the diamines mentioned are reacted in total (part amount from stage a) and part amount from stage b)) in those ratios of amounts which correspond to a ratio of the equivalents of isocyanate groups to amino groups of at least 4:1, preferably from 8:1 to 60:1 and particularly preferably from 16:1 to 50:1, the primary amino groups entering into the calculation as monofunctional groups. A ratio of equivalents of isocyanate groups to amino groups of from 18:1 to 25:1 is very particularly preferred. That is to say the number of NCO groups fed per unit time in total into a) and b) to the number of $NH_2$ groups fed in per unit time is at least 4:1, preferably 8:1 to 60:1, particularly preferably 16:1 to 50:1 and very particularly preferably 18:1 to 25:1.

The reaction in the process according to the invention can be catalysed and non-catalysed. If the process is carried out under catalysis, any desired acids, preferably proton acids, having a $pK_a$ value of <10 are preferably employed as catalysts, as described in EP-B 1158013. Preferred acid catalysts are phosphoric acid and phosphoric acid esters, such as e.g. methyl phosphate, ethyl phosphate, n-butyl phosphate, n-hexyl phosphate, 2-ethylhexyl phosphate, isooctyl phosphate, n-dodecyl phosphate, dimethyl phosphate, diethyl phosphate, di-n-propyl phosphate, di-n-butyl phosphate, di-n-amyl phosphate, diisoamyl phosphate, di-n-decyl phosphate, diphenyl phosphate or dibenzyl phosphate, sulfonic acids, such as e.g. methanesulfonic acid, ethanesulfonic acid, propanesulfonic acid, 2- or 4-toluenesulfonic acid or naphthalene-1-sulfonic acid, or also mono- and dicarboxylic acids, such as e.g. formic acid, acetic acid, propionic acid, butyric acid, pivalic acid, stearic acid, cyclohexanecarboxylic acid, oxalic acid, malonic acid, succinic acid, adipic acid, benzoic acid or phthalic acid. Dialkyl phosphates of the type mentioned are particularly preferred. Di-n-butyl phosphate is a very particularly preferred catalyst.

These acids are employed in the process according to the invention in amounts of from 0 to 1.0 wt. %, preferably from 0.02 to 0.5 wt. % and very particularly preferably from 0.05 to 0.5 wt. %, based on the total amount of the starting diisocyanates and the diamines employed. These acids can be added as a solution in a suitable solvent. The acids are preferably added in undissolved form.

The catalysed procedure is preferred over the non-catalysed procedure.

The process according to the invention is preferably carried out without a solvent. However, it is entirely possible also to co-use suitable solvents which are inert under the reaction conditions. Suitable solvents are, for example, hexane, ethyl acetate, butyl acetate, 1-methoxypropyl 2-acetate, propylene glycol diacetate, 2-butanone, 4-methyl-2-pentanone, cyclohexanone, toluene, xylene, more highly substituted aromatics, such as are commercially available, for example, under the names Solventnaphtha®, Solvesso®, Isopar®, Nappar® (Deutsche EXXON CHEMICAL GmbH, Köln) and Sheilsol® (Deutsche Shell Chemie GmbH, Eschborn), or trialkyl phosphates, such as e.g. trimethyl phosphate, and any desired mixtures of such solvents. The co-use of inert solvents is not preferred and these must be usable, if at all, under the reaction conditions with respect to amounts and boiling points.

For carrying out the process according to the invention, in the first stage the starting materials are reacted with one another at a temperature of above 170° C., preferably of from 200° C. to 320° C., in particular from 230 to 320° C., immediately after their mixing. For this, the first part stream of the isocyanate component A (stage a)), of which 10 to 90 parts by weight, preferably 40 to 80 parts by weight and particularly preferably 50 to 75 parts by weight of A per unit time are fed to the amine stream B, is preheated to temperatures above 150° C., preferably at least 180° C., particularly preferably 180 to 240° C. and very particularly preferably 200 to 240° C. Preferably, an excess of isocyanate groups of the isocyanate component A compared with the amine groups of the amine component B is present during metering a). In the case where a high excess of isocyanate is used, preheating of the diamines is often superfluous, but in general this is also preheated to approx. 50 to 200° C. As a rule, it can be assumed that immediately after its preparation by mixing of the starting materials, even in the absence of heating of the mixing vessel, because of the high evolution of heat of the spontaneously proceeding reaction the reaction mixture heats up to a temperature which is approx. 20 to 80° C. above the temperature which can be expected on the basis of the heating up of the starting materials without including the evolution of heat and which then corresponds to the abovementioned reaction temperature ranges.

The heating up and overheating of the isocyanates, which is necessary in all cases, must be effected within the shortest possible period of time. Preferably after a first heating up to a temperature still lower than the necessary temperature, where the mixing of step a) has to be done, the overheating to this temperature is done within a period of time of less than 30 seconds, because of the known heat sensitivity of these compounds. This is achieved by using appropriate heat exchanger units of the prior art. The heat exchangers can be designed e.g. as tubular, bundle or plate heat exchangers. Micro heat exchanger and microprofiled heat exchangers (MiProWa) can likewise be employed. They can be operated with a liquid heating medium, with superheated steam or with direct electrical heating. The use of those heat exchangers which allow the heating up operation on the starting diisocyanates within a period of time of less than 3 seconds is particularly preferred.

The continuous streams of the reaction partners are combined in a mixing chamber after the preheating described. Any desired static or dynamic units of the prior art can be employed. Simple mixing chambers configured as a simple reaction tube without any installed components, at one end of which the reaction components are introduced in co-current, can likewise be employed. Mixing units with a geometry optimized to the flow are preferred, in order to ensure the quality of the product and a high yield.

The entry point of the components and exit points of the reaction mixture are preferably constructed in the form of perforated plates or nozzles, so that the metering in can take place under increased pressure. It can be ensured by this means that the reaction mixture cannot enter into the diisocyanate and diamine feed lines. For this, the cross-sections are chosen such that a pressure of from 1.5 to 100 bar, preferably from 1.5 to 40 bar is in each case built up in the feed lines.

In the event of an additional metering of acids, this is expediently carried out in the region of the mixing chamber, preferably into the isocyanate component immediately before metering of the amine. Conventional pumps of the prior art, such as e.g. piston or piston membrane pumps, can be used for metering in the acids. It is merely necessary for the metering-in pressure to be higher than the mixing chamber pressure.

After passage through the mixing chamber and a dwell time zone which optionally follows, the 2nd part stream of the isocyanate component A (stage b)) is metered with 90 to 10 parts, preferably 60 to 20 parts and particularly preferably 50 to 25 parts per unit time into the reaction mixture.

The ratio of the parts by weight of the isocyanate component A fed per unit time into stage a) to stage b) is 1:9 to 9:1, preferably 4:6 to 8:2, particularly preferably 5:5 to 7.5:2.5.

The composition of the isocyanate stream in stage b) can be identical to or different from that of the isocyanate stream in stage a). In contrast to the isocyanate stream from a), conventionally no catalytically acting additions are added here. In principle, the isocyanate component of the isocyanate stream in b) can also be modified by prior preliminary reactions, such as urethanization, allophanation or trimerization. However, this is less preferred. Preferably, the isocyanate stream in b) is the same isocyanate as in the isocyanate stream in a). Particularly preferably, HDI is employed both as the isocyanate stream in a) and as the isocyanate stream in b).

No major requirements are imposed on the geometry of the metering zone. A simple tube feed (T-piece) or a nozzle or perforated disc are sufficient. In the case of turbulent flow, mixing baffles in the reaction tube can be dispensed with.

The temperature of the 2nd isocyanate part stream in stage b) is 20 to 250° C., particularly preferably 20, to 230° C. and very particularly preferably 100 to 220° C. The temperature of the 2nd isocyanate part stream in stage b) can be the same temperature as that of the 1st isocyanate part stream in stage a) as long as the temperature of the first part stream is a maximum of 250° C. However, the temperature of the second part stream is preferably below the temperature of the 1st part stream.

With the 2nd part stream, the overall temperature of the mixture established should preferably be below that of the first mixture of part stream 1, and amine stream. The temperature of the 2nd part stream should be chosen such that the overall temperature after the metering is less than 255° C., preferably less than 235° C. and particularly preferably between 235 and 170° C.

After the metering in of the 2nd isocyanate stream (stage b)), the dwell time of the hot reaction mixture up to the subsequent working up stage should be kept as short as possible, depending on the temperature which results. At temperatures of >235-255° C., the optimum dwell time is in the range of from 1 sec to 10 min, at a temperature of 200-235° C. the dwell time is in the range of between 30 sec and 120 min, and at temperatures of 170-<200° C. the dwell time is 10 min up to 8 h. The optimum dwell time must be determined for each installation.

Within the entire dwell time zone, cooling takes place usually continuously by suitable heat exchangers and pipelines. The temperature is cooled continuously by this means to a range of from 80 to 220° C., preferably 120 to 200° C., the abovementioned temperature/dwell time ranges being fulfilled for after-heating. Reactors arranged in the form of a cascade, for example, can also be located within the dwell time zone, in order to ensure an optimum mean dwell time. In a dwell time zone graduated from 220° C. to approx. 180° C., the optimum dwell time is approx. 30 min.

After the thermal after-treatment, a solution of polyisocyanates containing biuret groups in excess starting isocyanate and solvents optionally co-used, if these have not already been distilled off during the reaction, is present as the reaction product. The mixture present is then in general freed from volatile constituents (excess monomeric diisocyanates and solvents optionally co-used) by distillation under a high vacuum, preferably in a thin film evaporator, for example at a temperature of from 100 to 200° C., preferably from 120 to 180° C. Any desired suitable embodiments can be employed as evaporators in this context, such as flash evaporators, circulation evaporators, downpipe evaporators, falling film evaporators, thin film evaporators and molecular evaporators, which can optionally be connected stepwise in parallel or in series.

In a further embodiment of the process according to the invention, the volatile constituents mentioned can be separated off from the reaction product by extraction with suitable solvents which are inert towards isocyanate groups, for example aliphatic or cycloaliphatic hydrocarbons, such as pentane, hexane, heptane, cyclopentane or cyclohexane. If appropriate other extractans can be used as e.g. fluoro hydrocarbons. After the working up by extraction or distillation, high-quality polyisocyanates with a biuret structure which have a content of excess starting diisocyanate of a maximum of 0.5 wt. %, preferably of a maximum of 0.3 wt. % are obtained.

The polyisocyanates containing biuret groups prepared by the process according to the invention, in particular those which have been prepared using exclusively 1,6-diisocyanatohexane and 1,6-diaminohexane as starting materials, are valuable starting materials for the preparation of two-component polyurethane lacquers. The products prepared according to the invention, like the biuret polyisocyanates of the prior art known to date, have good colour numbers and comparatively low viscosities.

However, the proportion of side reactions (e.g. the uretonimine content obtained) is lower in the one-stage diisocyanate/diamine process, which favours the monomer stability of the polyisocyanate.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

In the following examples, all percentage data relate to percentages by weight and parts correspond to parts by weight.

The NCO content of the products described in the examples and comparison examples was determined by titration in accordance with DIN 53 185.

The dynamic viscosities were determined at 23° C. with a Physica MCR 51 viscometer, Anton Paar, Graz, AT. By measurements at different shear rates it was ensured that the flow properties of the polyisocyanates prepared according to the invention which are described, like also those of the comparison products, correspond to Newtonian fluids. It is therefore not necessary to state the shear rate.

Example 1

4,600, parts of hexamethylene-diisocyanate (HDI) per hour were passed continuously through a reaction mixing chamber at 214° C. in an experimental apparatus for the continuous preparation of biuret polyisocyanates. A continuous stream of 10 parts of di-n-butyl phosphate (DBP) per hour was additionally injected into the HDI feed line shortly before the mixing chamber. 270 parts of hexamethylenediamine (HDA) per hour were now fed, likewise continuously, into this mixing chamber, the temperature in the mixing chamber rising to 255° C. due to the heat of reaction. After leaving the mixing chamber, 2,076 parts of HDI with a temperature of 136° C. were added to the product. A temperature of 222° C. was established by this means. The mixture was cooled to 180° C. by further external cooling in the course of approx. 2 minutes. It was after-heated at this temperature for a further 30 minutes and the crude product was allowed to flow into an intermediate container. With the aid of the conventional thin film distillation technique, excess HDI was then separated off from the crude product obtained in this way. A biuret polyisocyanate which is suitable as a paint hardener and has the following characteristic data was obtained:
NCO: 22.0%
Viscosity: 9,500 mPas (23° C.)

Example 2

4,600 parts of hexamethylene-diisocyanate (HDI) per hour were passed continuously through a reaction mixing chamber at 214° C. in an experimental apparatus for the continuous preparation of biuret polyisocyanates. A continuous stream of 10 parts of di-n-butyl phosphate (DBP) per hour was additionally injected into the HDI feed line shortly before the mixing chamber. 270, parts of hexamethylenediamine (HDA) per hour were now fed, likewise continuously, into this mixing chamber, the temperature in the mixing chamber rising to 255° C. due to the heat of reaction. After leaving the mixing chamber, 2,076 parts of HDI with a temperature of 170° C. were added to the product and the mixture was heated at 230° C. for 90 seconds. Thereafter, it was cooled to <180° C. by external cooling in the course of approx. 2 minutes and transferred into an intermediate container. With the aid of the conventional thin film distillation technique, excess HDI was then separated off from the crude product obtained in this way. A biuret polyisocyanate which is suitable as a paint hardener and has the following characteristic data was obtained:
NCO: 22.1%
Viscosity: 9,300 mPas (23° C.)

Comparison Example 1

Comparison According to EP-B 1158013

6,670 parts of hexamethylene-diisocyanate (HDI) per hour were passed continuously through a reaction mixing chamber at 250° C. in an experimental apparatus for the continuous preparation of biuret polyisocyanates. A continuous stream of 10, parts of di-n-butyl phosphate (DBP) per hour was additionally injected into the HDI feed line shortly before the mixing chamber. 270 parts of hexamethylenediamine (HDA) per hour were now fed, likewise continuously, into this mixing chamber, the temperature in the mixing chamber rising to 280° C. due to the heat of reaction. After leaving the mixing chamber, the product was cooled to 180° C. in the course of a few seconds and after-heated at 180-140° C. for some further minutes. With the aid of the conventional thin film distillation technique, excess HDI was then separated off from the crude product obtained in this way. A biuret polyisocyanate which is suitable as a paint hardener and has the following characteristic data was obtained:
NCO: 21.8%
Viscosity: 11,100 mPas (23° C.)

Comparison Example 2 Comparison According to EP-B 1158013

As described in Comparison Example 1, the mass flow of HDI is passed continuously into the mixing chamber at 230° C., DBP is added and HDA is fed in continuously. The temperature in the mixing chamber rises to approx. 260° C. and, after cooling, after-heating and working up, a biuret polyisocyanate with the following characteristic data is obtained:
NCO: 22.1%
Viscosity: 9,520 mPas (23° C.)

As Examples 1 and 2 and Comparison Examples 1 and 2 demonstrate, only in each case 4,600 parts of HDI per hour have to be heated to 214° C. in the examples according to the invention, whereas in the comparison examples 6,670 parts of HDI have to be heated to 250° C. or at least 230° C. The process according to the invention allows a significant saving of energy.

Example 3

6,670 parts of hexamethylene-diisocyanate (HDI) per hour were passed continuously through a reaction mixing chamber at 225° C. in an experimental apparatus for the continuous preparation of biuret polyisocyanates. A continuous stream of 10 parts of di-n-butyl phosphate (DBP) per hour was additionally injected into the HDI feed line shortly before the mixing chamber. 270 parts of hexamethylenediamine (HDA) per hour were now fed, likewise continuously, into this mixing chamber, the temperature in the mixing chamber rising to 255° C. due to the heat of reaction. After leaving the mixing chamber, 5,090 parts of HDI with a temperature of 85° C. were added to the product and the mixture was thus cooled to 180° C. It was after-heated at this temperature for a further 2 hours and the crude product was then transferred into an intermediate container. With the aid of the conventional thin film distillation technique, excess HDI was then separated off from the crude product obtained in this way. A biuret polyisocyanate which is suitable as a paint hardener and has the following characteristic data was obtained:

NCO: 23.5%

Viscosity: 2,700 mPas (23° C.)

This Example 3 shows that in the preparation of a biuret polyisocyanate of comparatively low viscosity, only 6,670 parts (57%) of in total 11,760 parts of HDI have to be heated to the high temperature of 225° C. At the same time, the HDI/HDA ratio of the first reaction stage can be established without problems in the same apparatus with the same nozzle sizes as Examples 1 and 2 and the comparison examples.

As stated in EP-B 1158013, additions of acids, such as, for example, dibutyl phosphate, have the effect of accelerating the reaction, contribute towards the monomer stability of the products and reduce the sensitivity of the products to damp solvents. Larger amounts (0.05-0.5%), compared with 0.02-0.5%, are particularly preferred in the reaction here (see page 3, and 4) In EP-B 1158013, 0.15 wt. % of DBP is used in Ex. 6a, but 0.25 wt. % of DBP is used in Ex. 7a. As already described there, the higher addition of acid has a particularly advantageous effect, as the monomeric HDI contents after storage for 1 week/80° C. demonstrate: 0.45% of HDI at a 0.25 wt. % addition of DBP compared with 0.58% of HDI at a 0.15 wt. % addition. In the process according to the invention, it is thus possible to maximize the DBP concentration in the first reaction step a) without increasing the total amount of DPB based on the amount of starting material employed in total in the process. The positive effects described in EP-B 1158013, can thus be utilized without having to exceed the 1.0 wt. %, preferably 0.5 wt. % addition of acid and without contaminating the biuret polyisocyanate too much with traces of secondary products.

The invention claimed is:

1. A process for continuously preparing a polyisocyanate comprising a biuret structure comprising continuously reacting an excess amount of an organic isocyanate (A) comprising exclusively aliphatically and/or cycloaliphatically bonded isocyanate groups with an organic amine (B) comprising exclusively aliphatically and/or cycloaliphatically bonded primary amino groups by
 a) mixing a first amount of said organic isocyanate (A) with said organic amine (B) at a temperature above 170° C. to form a reaction mixture stream, and
 b) metering a second amount of said organic isocyanate (A) at a temperature in the range of from 20 to 250° C. into said reaction mixture stream of a),
wherein
the ratio of the parts by weight of said organic isocyanate (A) fed per unit time into step a) to the parts by weight of said organic isocyanate (A) fed per unit time into b) is in the range of from 1:9 to 9:1, and
the ratio of the total number of NCO groups fed per unit time into both steps a) and b) to the number of $NH_2$ groups fed in per unit time into step a) is at least 4:1.

2. The process of claim 1, wherein said organic isocyanate (A) comprises HDI.

3. The process of claim 1, wherein said organic amine (B) comprises HDA.

4. The process of claim 1, wherein the ratio of the total number of NCO groups fed per unit time into both steps a) and b) to the number of $NH_2$ groups fed in per unit time into step a) is in the range of from 18:1 to 25:1.

5. The process of claim 1, wherein the ratio of the parts by weight of said organic isocyanate (A) fed per unit time into step a) to the parts by weight of said organic isocyanate (A) fed per unit time into b) is in the range of from 5:5 to 7.5:2.5.

6. The process of claim 1, wherein said first amount of said organic isocyanate (A) in step a) is preheated to a temperature in the range of from 200 to 240° C. before it is mixed with said organic amine (B).

7. The process of claim 1, wherein the temperature in step a) is maintained in the range of from 230 to 320° C.

8. The process of claim 1, wherein said second amount of said organic isocyanate (A) in step b) has a temperature below that of said first amount of said organic isocyanate (A) in step a).

9. The process of claim 1, wherein said process is carried in the presence of a catalyst.

10. The process of claim 9, wherein said catalyst comprises one or more acids or mixtures thereof.

11. The process of claim 10, wherein said catalyst comprises di-n-butyl phosphate.

12. The process of claim 1, wherein said polyisocyanate comprising a biuret structure is purified from excess monomeric diisocyanate via extraction or thin film distillation resulting in a monomeric diisocyanate content of less than 0.5 wt. %.

* * * * *